United States Patent
Oomori et al.

(10) Patent No.: US 12,100,600 B2
(45) Date of Patent: Sep. 24, 2024

(54) DRY ETCHING METHOD, AND DRY ETCHING AGENT AND STORAGE CONTAINER THEREFOR

(71) Applicant: Central Glass Company, Limited, Ube (JP)

(72) Inventors: Hiroyuki Oomori, Ube (JP); Tatsunori Kamida, Ube (JP); Shinya Ikeda, Ube (JP)

(73) Assignee: CENTRAL GLASS COMPANY, LIMITED, Ube (JP)

( * ) Notice: Subject to any disclaimer, the term of this patent is extended or adjusted under 35 U.S.C. 154(b) by 552 days.

(21) Appl. No.: 17/424,211

(22) PCT Filed: Dec. 20, 2019

(86) PCT No.: PCT/JP2019/049999
§ 371 (c)(1),
(2) Date: Jul. 20, 2021

(87) PCT Pub. No.: WO2020/153066
PCT Pub. Date: Jul. 30, 2020

(65) Prior Publication Data
US 2022/0115240 A1    Apr. 14, 2022

(30) Foreign Application Priority Data
Jan. 23, 2019  (JP) ................ 2019-008990

(51) Int. Cl.
*H01L 21/31* (2006.01)
*C09K 13/02* (2006.01)
(Continued)

(52) U.S. Cl.
CPC ........ *H01L 21/31116* (2013.01); *C09K 13/02* (2013.01); *C09K 13/08* (2013.01);
(Continued)

(58) Field of Classification Search
CPC .................. C09K 13/00; H01L 21/31116
See application file for complete search history.

(56) References Cited

U.S. PATENT DOCUMENTS 6,177,147 B1   1/2001   Samukawa et al.
6,977,316 B1   12/2005  Mukhopadhyay et al.
(Continued)

FOREIGN PATENT DOCUMENTS

JP   11-340211 A      12/1999
JP   2008-523089 A    7/2008
(Continued)

OTHER PUBLICATIONS

Donnelly et al. CF3I Stability Under Storage. NIST Technical Note 1452. 2004 (Year: 2004).*

(Continued)

*Primary Examiner* — Cachet I Proctor
(74) *Attorney, Agent, or Firm* — Crowell & Moring LLP

(57) ABSTRACT

A dry etching method according to one embodiment of the present disclosure includes plasmatizing a dry etching agent and etching a silicon oxide or a silicon nitride with the plasmatized dry etching agent, wherein the dry etching agent comprises $CF_3I$ and a C2-C3 fluorine-containing linear nitrile compound, and wherein the concentration of the C2-C3 fluorine-containing linear nitrile compound relative to the $CF_3I$ is higher than or equal to 1 vol. ppm and lower than or equal to 1 vol %.

8 Claims, 1 Drawing Sheet

10. Storage Test Container
12. Valve
14. Pressure-Resistant Vessel

(51) Int. Cl.
*C09K 13/08* (2006.01)
*H01L 21/3065* (2006.01)
*H01L 21/311* (2006.01)
*C07C 17/093* (2006.01)
*C07C 17/361* (2006.01)
*C07C 19/08* (2006.01)

(52) U.S. Cl.
CPC .... *H01L 21/3065* (2013.01); *H01L 21/31138* (2013.01); *C07C 17/093* (2013.01); *C07C 17/361* (2013.01); *C07C 19/08* (2013.01)

(56) References Cited

U.S. PATENT DOCUMENTS

| | | | | |
|---|---|---|---|---|
| 2007/0282142 A1* | 12/2007 | Ohmi | ..................... | C23C 4/11 570/124 |
| 2008/0191163 A1* | 8/2008 | Mocella | .................. | C07C 21/18 570/175 |
| 2009/0123875 A1 | 5/2009 | Soda | | |
| 2009/0246967 A1* | 10/2009 | Yaguchi | ............ | H01L 21/31111 252/79.3 |
| 2015/0079789 A1* | 3/2015 | Mori | ..................... | B24B 37/044 438/693 |
| 2015/0371869 A1* | 12/2015 | Surla | .................. | H01L 21/0271 558/461 |
| 2017/0110336 A1* | 4/2017 | Hsu | ..................... | H01L 21/31144 |
| 2017/0178923 A1* | 6/2017 | Surla | ................ | H01L 21/31116 |
| 2018/0211845 A1* | 7/2018 | Hsu | ..................... | H01L 21/3081 |
| 2019/0055469 A1 | 2/2019 | Hyakutake | | |

FOREIGN PATENT DOCUMENTS

| | | | |
|---|---|---|---|
| JP | 2009-123866 A | 6/2009 | |
| WO | WO-2017159544 A1 * | 9/2017 | ............. C07C 19/08 |

OTHER PUBLICATIONS

International Search Report (PCT/ISA/210) issued in PCT Application No. PCT/JP2019/049999 dated Mar. 3, 2020 with English translation (four (4) pages).

Japanese-language Written Opinion (PCT/ISA/237) issued in PCT Application No. PCT/JP2019/049999 dated Mar. 3, 2020 (four (4) pages).

* cited by examiner

DRY ETCHING METHOD, AND DRY ETCHING AGENT AND STORAGE CONTAINER THEREFOR

TECHNICAL FIELD

The present disclosure relates to a method of plasma etching a silicon-based material, a dry etching agent used in such an etching method, and a storage container of the dry etching agent.

In recent years, there have been made studies on fine processing techniques for processing of semiconductors. In these techniques, there is a tendency to not only decrease the processing line width, but also significantly increase the aspect ratio which denotes the ratio of the processing line width to the trench/hole depth. With the development of the semiconductor processing techniques, the development of etching agents used in etching processes has also been pursued.

An etching device using plasmas is widely applicable to the etching processes. In the etching processes, it is required to use processing gases each capable of etching only a $SiO_2$ film or SiN film relative to a PR film or a-C film at a high selectivity e.g. selectivity ratio of 3.0 or higher and at a high rate e.g. $SiO_2$ etching rate of 50 nm/min or higher.

As such etching gases, fluorine-containing saturated hydrocarbons or fluorine-containing unsaturated hydrocarbons, as typified by $CF_4$ gas, c-$C_4F_8$ gas and $C_4F_6$ gas, are conventionally known. However, the conventional gases are becoming difficult to adapt to the recent fine processing techniques because each of the conventional gases cannot attain a sufficient etching selectivity, cannot maintain a linearity in etching shape during the processing or cannot attain a sufficient etching rate.

Further, the fluorine-containing saturated hydrocarbons have a long atmospheric lifetime and a high global warning potential (GWP) and thus are specified as emission control materials in the Kyoto protocol (COP3). In the semiconductor industry, there has been a demand to for alternative materials high in economic efficiency, capable of fine processing and low in GWP.

Patent Document 1 discloses an etching method using $CF_3I$, as a gas satisfying the above-mentioned requirements, so as to generate a desired amount of desired radicals or ions for high aspect ratio etching. Patent Document 2 discloses that $CF_3I$ provides a higher etching selectivity ratio between a resist layer and a silicon-containing layer (such as organic silicon oxide layer) than that of $CF_4$.

Patent Document 3 discloses a method of producing $CF_3I$ by reacting a predetermined iodine source with a reactant of the formula: $CF_3R$ in the presence of a metal salt catalyst.

PRIOR ART DOCUMENTS

Patent Documents

Patent Document 1: Japanese Laid-Open Patent Publication No. 1111-340211

Patent Document 2: Japanese Laid-Open Patent Publication No. 2009-123866

Patent Document 3: Japanese Translation of International Patent Application No. 2008-523089 (also published as International Patent Publication No. 2006/063184)

SUMMARY OF THE INVENTION

In general, a metal container with a metal valve is commonly used for storing a high pressure liquefied gas of $CF_3I$ or the like. Since $CF_3I$ is known as a stable compound, stainless steel, carbon steel, brass, manganese steel etc. are often utilized as the materials of the container and the valve in view of cost advantage. The present inventors have however found that, when a high-purity $CF_3I$ gas obtained by purifying $CF_3I$ to 99.99 vol % or higher is charged into a cylinder of manganese steel and practically used as an etching gas, the use of such a high-purity $CF_3I$ gas leads to expected results in terms of etching rate and etching shape but results in the occurrence of metal contamination on a wafer during the etching.

The occurrence of metal contamination on the wafer causes an influence on semiconductor properties. It is thus required in the development of etching gases to minimize the amount of metal contamination on the wafer during the semiconductor manufacturing process, in addition to improving the etching shape and the etching selectivity to the mask material, even though the metal contamination amount cannot be reduced to 0. On the other hand, none of Patent Documents 1 to 3 make a mention about the purity and impurity of $CF_3I$ and the occurrence of metal contamination on the wafer.

Against the foregoing backdrop, there has been a demand to develop an etching method using $CF_3I$, in which the amount of metal contamination is reduced without causing an influence on etching characteristics.

Under such circumstances, the present inventors have made studies on the causes of metal contamination, and resultantly found that a storage container filled with highly purified $CF_3I$ is a cause of metal contamination and, more specifically, a trace amount of metal contaminant is contained in the form of a fluoride or iodide by contact of the $CF_3I$ with the container material such as manganese steel or stainless steel. As a result of further intensive studies, the present inventors have found that: the occurrence of metal contamination from the storage container of the $CF_3I$ is suppressed by the addition of a predetermined amount of a C2-C3 fluorine-containing linear nitrile compound with a C≡N bond to the $CF_3I$; and an etching process using such a mixed gas provides a sufficient etching selectivity between PR and $SiO_2$ and a good etching shape. The present disclosure is accomplished based on these findings.

Accordingly, the present disclosure is directed to a dry etching method comprising: plasmatizing a dry etching agent; and etching a silicon oxide or a silicon nitride with the plasmatized dry etching agent, wherein the dry etching agent comprises $CF_3I$ and a fluorine-containing linear nitrile compound of 2 or 3 carbon atoms, and wherein a concentration of the fluorine-containing linear nitrile compound relative to the $CF_3I$ is higher than or equal to 1 vol. ppm and lower than or equal to 1 vol %.

DETAILED DESCRIPTION OF THE EMBODIMENTS

Figure 1:
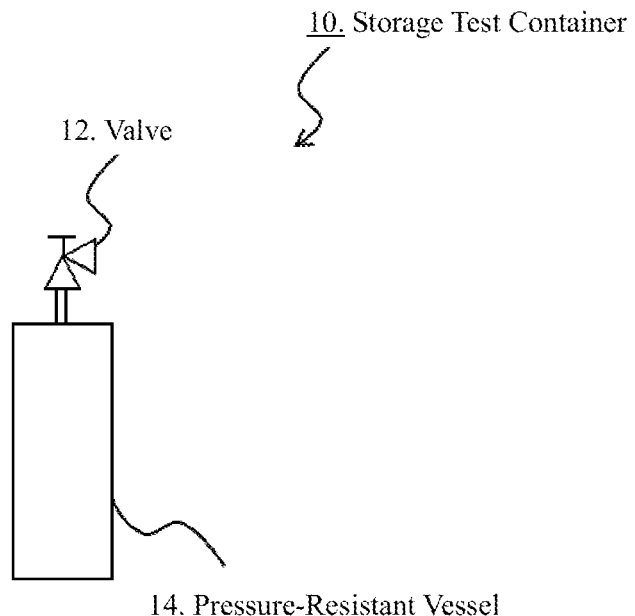
FIG. 1 is a schematic view of a storage test container used in Examples and Comparative Examples.

Hereinafter, embodiments of the present disclosure will be described below. It is to be understood that the scope of the present disclosure is not limited to the following embodiments; and changes and modifications can be appropriately made to the following embodiments within the range that does not impair the effects of the present disclosure.

A dry etching method according to the present embodiment includes the steps of: plasmatizing a dry etching agent; and etching a silicon oxide or silicon nitride with the plasmatized dry etching agent. The dry etching agent includes at least $CF_3I$ and a C2-C3 fluorine-containing linear nitrile compound with a C≡N bond.

The $CF_3I$ used in the present embodiment is also called trifluoroiodomethane or trifluoromethyl iodide, and can be produced by a conventionally known method. For example, it is feasible according to Patent Document 3 to obtain $CF_3I$ by reacting an iodine source selected from the group consisting of hydrogen iodide, iodine and iodine monochloride with a reactant of the formula: $CF_3R$ (where R is selected from the group consisting of —SH, —S—S—$CF_3$, —S-phenyl and —S—S—$(CH_3)_3$) in the presence of a metal salt catalyst.

Examples of the C2-C3 fluorine-containing linear nitrile compound used in the present embodiment include $CH_2FC≡N$, $CHF_2C≡N$, $CF_3C≡N$, $CH_2FCF_2C≡N$, $CHF_2CF_2C≡N$, $CF_3CF_2C≡N$ and the like. Among others, $CF_3C≡N$ and $CF_3CF_2C≡N$ are preferred. A sufficient metal contamination suppressing effect is recognized when the the amount of the C2-C3 fluorine-containing linear nitrile compound added relative to the $CF_3I$ is higher than or equal to 1 vol. ppm.

On the other hand, attention is now given to the factor having an influence on the etching characteristics. Patent Document 1 suggests the possibility that a trace amount of impurity contained in the $CF_3I$ may serve as a source of generation of radical species other than intended radical species and thereby cause an effect on the etching characteristics, but discloses that the etching characteristics are not largely influenced by such a trace amount of impurity. However, too large amount of impurity causes some influence on the etching performance of the $CF_3I$. Thus, the amount of the fluorine-containing linear nitrile compound added is preferably lower than or equal to 1 vol % (10000 vol. ppm), more preferably lower than or equal to 0.1 vol % (1000 vol. ppm). In another embodiment of the present disclosure, it is conceivable to previously seal the C2-C3 fluorine-containing linear nitrile compound in a container and perform passivation treatment on an inner surface of the container.

The silicon oxide is represented by the chemical formula: $SiO_x$ (where x is greater than or equal to 1 and smaller than or equal to 2). A typical example of the silicon oxide is $SiO_2$. The silicon nitride is represented by the chemical formula: $SiN_x$ (where x is greater than or equal to 0.3 and smaller than or equal to 9). A typical example of the silicon nitride is $Si_3N_4$.

As a storage container of the $CF_3I$, there is used any closed container capable of sealing therein a gas-liquid mixture at a pressure higher than or equal to atmospheric pressure. The storage container of the $CF_3I$ does not require a special structure and material and can have a wide range of forms and functions. The present disclosure is applicable to the case where an ordinary high-pressure gas storage container such as cylinder made of manganese steel or stainless steel is used as the storage container.

It is preferable that the manganese steel has an iron content of 97 mass % or higher and a manganese content of 1 mass % to 2 mass %. When nickel and chromium are unavoidably contained in the manganese steel, it is preferable that the manganese steel has a nickel content of 0.25 mass % or lower and a chromium content of 0.35 mass % or lower. Examples of the manganese steel are: SMn420, SMn433 and SMn438, all of which are specified in JIS G 4053:2016; STH11 and STH12, both of which are specified in JIS G 3429:2013; and the like.

In the present embodiment, it is preferable that the $CF_3I$ used is purified to a high purity of 99.95 vol % or higher. It is acceptable that the purity of the C2-C3 fluorine-containing linear nitrile compound is 90 vol % or higher as long as a predetermined amount of the C2-C3 fluorine-containing linear nitrile compound is contained in the dry etching agent.

Next, the dry etching method using the dry etching agent according to the present embodiment will be explained in more detail below.

The dry etching agent is a mixed gas of the $CF_3I$ and the fluorine-containing linear nitrile compound with or without an additive gas and/or an inert gas. The preferable composition of the dry etching agent is as follows. Herein, the total amount of the respective gas components in units of vol % is assumed as 100 vol %.

The mixed gas of the $CF_3I$ and the fluorine-containing linear nitrile compound is generally used in combination with the additive gas and/or the inert gas in view of cost-effectiveness and plasma stability although the mixed gas of the $CF_3I$ and the fluorine-containing linear nitrile compound can be used solely as the dry etching agent. The concentration of the mixed gas of the $CF_3I$ and the fluorine-containing linear nitrile compound is preferably 1 to 90 vol %, more preferably 5 to 80 vol %, still more preferably 10 to 60 vol %, based on the total amount of the mixed gas, the additive gas and the inert gas.

The concentration of the additive gas is preferably 0 to 50 mass %, more preferably 0 to 10 vol %, based on the total amount of the mixed gas, the additive gas and the inert gas.

The concentration of the inert gas is preferably 0 to 98 mass %, more preferably 5 to 80 mass %, still more preferably 30 to 50 vol %, based on the total amount of the mixed gas, the additive gas and the inert gas.

The etching method according to the present embodiment can be carried out under various dry etching conditions. Further, various additives and inert gases can be added so as to achieve a desired etching rate, etching selectivity and etching shape. As the additive gas, at least one kind of gas selected from the group consisting of $O_2$, $O_3$, CO, $CO_2$, $COCl_2$, $COF_2$, $CF_2(OF)_2$, $CF_3OF$, $NO_2$, NO, $F_2$, $NF_3$, $Cl_2$, $Br_2$, $I_2$ and $YF_n$ (where Y is Cl, Br or I; and n is an integer satisfying 1≤n≤7) is usable. In order to obtain a desired etching shape and etching rate, the etching step may be performed by using as the additive gas at least one kind of gas selected from reducing gases, fluorocarbons, hydrofluorocarbons and halogen-containing compounds (for example, at least one kind of gas selected from the group consisting of $H_2$, HF, HI, HBr, HCl, $NH_3$, $CF_4$, $CF_3H$, $CF_2H_2$, $CFH_3$, $C_2F_6$, $C_2F_4H_2$, $C_2F_5H$, $C_3F_8$, $C_3F_7H$, $C_3F_6H_2$, $C_3F_5H_3$, $C_3F_4H_4$, $C_3F_3H_5$, $C_3F_5H$, $C_3F_3H$, $C_3ClF_3H$, $C_4F_8$, $C_4F_6$, $C_5F_8$, $C_5F_{10}$, $C_3F_6$, $C_3HF_5$, $C_3H_2F_4$ and $C_3H_3F_3$). As the inert gas, $N_2$, Fe, Ar, Ne, Kr and Xe are usable.

The etching method according to the present embodiment can be carried out by various etching processes, such as capacitively coupled plasma (CCP) etching, reactive ion etching (RIE), inductively coupled plasma (ICP) etching, electron cyclotron resonance (ECR) plasma etching and microwave etching, with no particular limitations.

It is feasible to individually introduce the gas components of the dry etching agent into a chamber, or feasible to mix the gas components of the dry etching agent in advance at a stage downstream of the storage container and introduce the resulting mixed gas into a chamber. The total amount of the dry etching agent introduced into the reaction chamber is set as appropriate according to the capacity of the reaction chamber and the gas discharge performance of gas discharge equipment in consideration of the aforementioned concentration conditions and the undermentioned pressure conditions.

In order to obtain a stable plasma and to increase ion straightness and thereby suppress side etching, the pressure during the etching step is preferably 5 Pa or lower, more preferably 1 Pa or lower. When the pressure inside the chamber is too low, the amount of ionized ions becomes small so that a sufficient plasma density cannot be obtained. Thus, the pressure during the etching step is preferably 0.05 Pa or higher.

The substrate temperature during the etching step is preferably 100° C. or lower. The substrate temperature during the etching step is more preferably 50° C. or lower, still more preferably 20° C. or lower, for anisotropic etching. Under high temperature conditions exceeding 100° C., a fluorocarbon-derived protective film predominantly composed of $CF_n$ is not sufficiently formed on the mask material such as PR, a-C etc. so that the etching selectivity may be decreased. Further, there may occur a shape anomaly, so called a bowing phenomenon in which the etching shape becomes rounded due to insufficient formation of a sidewall protecting film, under high temperature conditions.

The negative direct-current self-bias voltage applied between electrodes during the etching step is set according to a desired etching shape. For example, it is preferable to allow high energization of ions by applying between the electrodes a negative direct-current self-bias voltage whose absolute value ranges from about 500 V to 10000 V. When the absolute value of the negative direct-current self-bias voltage is too large, the etching selectivity may be deteriorated with amplification of energy of ions.

In view of the efficiency of the element manufacturing process, the etching time is preferably 200 minutes or shorter. Herein, the "etching time" refers to the time in which the dry etching agent is plasmatized in the chamber and reacted with the etching target.

EXAMPLES

Hereinafter, Examples of the present disclosure will be described below along with Comparative Examples. It is to be understood that the present disclosure is not limited to the following Examples.

Example 1

(Storage in Storage Container)

FIG. 1 is a schematic view of a storage container 10 used for temporary storage of purified $CF_3I$ in each of Examples and Comparative Examples. The storage container used was a pressure-resistant container 10 made of manganese steel and having an internal volume of 10 L. In this storage container, 1000 g of highly purified $CF_3I$ which was previously purified to 99.99 vol % or higher was sealed. Then, $CF_3C\equiv N$ was added in an amount of 2 vol. ppm to the $CF_3I$.

(Etching Test)

Figure 2:
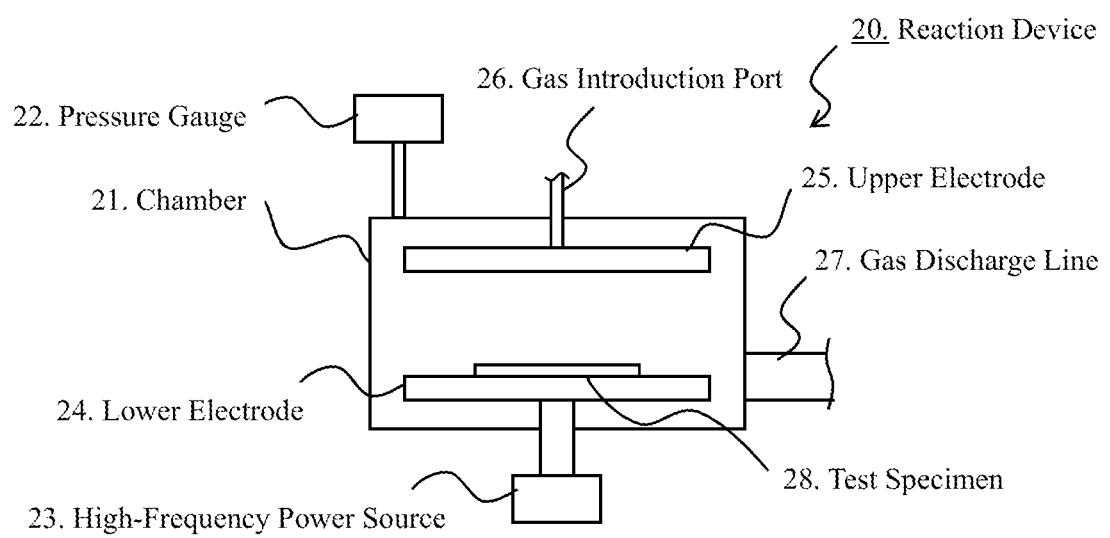
FIG. 2 is a schematic view of a reaction device used in Examples and Comparative Examples.

An etching test was conducted using the above-prepared mixed gas of $CF_3I$ and $CF_3C\equiv N$ in order to examine the influence of the additive on the etching characteristics. FIG. 2 is a schematic view of a reaction device used in each of Examples and Comparative Examples. A lower electrode 24 having a wafer holding function to serve as a stage, an upper electrode 25 and a pressure gauge 22 were disposed in a chamber 21 of the reaction device. A gas introduction port 26 is connected to an upper portion of the chamber 21. The chamber 21 was configured to adjust the internal pressure thereof and to excite the dry etching agent into a plasma by means of a high-frequency power source 23 (13.56 MHz). The excited dry etching agent was brought into contact with a test specimen 28 placed on the lower electrode 24 whereby the test specimen 28 was subjected to etching. When a high-frequency power was applied by the high-frequency power source 23 in a state that the dry etching agent was introduced into the chamber, there was developed a direct-current voltage called a self-bias voltage between the upper electrode 25 and the lower electrode 24 due to a transfer speed difference between ions and electrons in the plasma. The gas inside the chamber 21 was discharged through a gas discharge line 27.

As the test specimen 28, a silicon wafer A with a $SiO_2$ film, a silicon wafer with a SiN ($Si_3N_4$) film or a silicon wafer with a PR (photoresist) film was set on the stage which was cooled at 15° C. Each of the $SiO_2$ film and the SiN film was formed by a CVD process. The PR film was formed by application. The mixed gas of $CF_3I$ and $CF_3C\equiv N$, $O_2$ and Ar were supplied at flow rates of 25 sccm, 25 sccm and 500 sccm, respectively. The test specimen was etched by feeding the resulting well-mixed gas as the etching agent into the chamber and applying a high-frequency power of 400 W between the electrodes.

After the etching, the etching rates were respectively determined from changes in the thicknesses of the $SiO_2$ film on the silicon wafer A, the SiN film on the silicon wafer B and the PR film on the PR film before and after the etching. Further, the etching selectivity ratio was determined by dividing the etching rate of the $SiO_2$ film or the SiN film by the etching rate of the PR film.

(Measurement of Metal Amount on Wafer)

Next, the amount of metal deposit on the $SiO_2$ film-coated silicon wafer A was measured. The measurement was made by a method specified in JIS K0160:2009. More specifically, a plastic beaker in which hydrofluoric acid was put was placed in a container of PFA (perfluoroalkoxy fluororesin) called a VPD (vapor phase decomposition) container. The $SiO_2$ film-coated wafer after the etching was set on a wafer stand inside the PVD container. Then, the VPD container was closed. In this state, the oxide film on the wafer was subjected to decomposition with a vapor of the hydrofluoric acid for 10 minutes. Subsequently, 100 μL of a scan liquid (ultrapure water) was dropped onto a surface of the wafer after the decomposition of the oxide film. The whole surface of the wafer was then scanned. After the scanning, the scanned liquid was entirely dried. The resulting residue was again dissolved in ultrapure water. The thus-obtained solution was analyzed by an ICP-MS (inductively coupled plasma-mass spectrometry). The analysis value was converted to the number of metal atoms per 1 $cm^2$ of the wafer on the basis of the amount of the solution and the surface area of the wafer. As a result, the analysis result of the iron deposit was found to be $6.5 \times 10^{11}$ atms/$cm^2$.

(Etching Shape Evaluation)

After the above-mentioned etching test, each of the wafers A to C was taken out. A wafer D for etching shape evaluation was set on the stage. The wafer D used was provided by forming a $SiO_2$ film of 200 nm thickness on a silicon wafer and applying a photoresist film of 300 nm thickness with a circular hole opening of 100 nm diameter onto the oxide film. The wafer was subjected to etching for 5 minutes by the method described in the section of "Etching Test". By taking a cross-sectional SEM photograph of the wafer, the etching shape was observed. As a result, it was confirmed that the etching was performed without causing an etching shape anomaly such as shoulder loss or bowing.

Example 2

A storage test sample was prepared under the same conditions as in Example 1, except that $CF_3C\equiv N$ was added in an amount of 25 vol. ppm to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Example 3

A storage test sample was prepared under the same conditions as in Example 1, except that $CF_3C\equiv N$ was added in an amount of 129 vol. ppm to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Example 4

A storage test sample was prepared under the same conditions as in Example 1, except that $CF_3C\equiv N$ was added in an amount of 1231 vol. ppm (about 0.1 vol %) to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Example 5

A storage test sample was prepared under the same conditions as in Example 1, except that $CF_3C\equiv N$ was added in an amount of 7927 vol. ppm (about 0.8 vol %) to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Example 6

A storage test sample was prepared under the same conditions as in Example 1, except that $CF_3C\equiv N$ was added in an amount of 9328 vol. ppm (about 0.9 vol %) to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Example 7

A storage test sample was prepared under the same conditions as in Example 1, except that $CF_3CF_2C\equiv N$ was added in an amount of 235 vol. ppm to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Comparative Example 1

A storage test sample was prepared under the same conditions as in Example 1, except that $CF_3C\equiv N$ was added in an amount of less than 0.1 vol. ppm to purified $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Comparative Example 2

A storage test sample was prepared under the same conditions as in Example 1, except that $CF_3C\equiv N$ was added in an amount of 25936 vol, ppm (about 2.6 vol %) to $CF_3I$. Further, an etching test was conducted in the same manner as in Example 1. The etching shape of the test specimen was then evaluated in the same manner as in Example 1. It was confirmed that, as compared to Examples 1 to 6, the etching amount of the PR film was increased with decrease in the $SiO_2$/PR selectivity ratio even though there was not seen an etching shape anomaly such as shoulder loss or bowing.

Comparative Example 3

A storage test sample was prepared under the same conditions as in Example 1, except that $CF_3C\equiv N$ was added in an amount of 111608 vol. ppm (about 11 vol %) to $CF_3I$. Further, an etching test was conducted in the same manner as in Example 1. The etching shape of the test specimen was then evaluated in the same manner as in Example 1. It was confirmed that, with decrease in the $SiO_2$/PR selectivity ratio, the etching amount of the PR film was significantly increased as compared to Examples 1 to 6 whereby there was seen no bowing, but was seen a shoulder loss in a part of the pattern.

Comparative Example 4

A storage test sample was prepared under the same conditions as in Example 1, except that $CF_3C\equiv CH$ was added in an amount of 28 vol. ppm, in place of $CF_3C\equiv N$, to $CF_3I$. Further, an etching test was conducted in the same manner as in Example 1. When the etching shape of the test specimen was evaluated in the same manner as in Example 1, it was confirmed that the etching was performed without causing an etching shape anomaly such as shoulder loss or bowing.

Comparative Example 5

A storage test sample was prepared under the same conditions as in Example 1, except that a fluorine-free nitrile compound $CH_3C\equiv N$ was added in an amount of 8523 vol. ppm, in place of $CF_3C\equiv N$, to $CF_3$. Further, an etching test was conducted in the same manner as in Example 1. The etching shape of the test specimen was then evaluated in the same manner as in Example 1. It was confirmed that, as compared to Examples 1 to 6, as compared to Examples 1 to 6, the etching amount of the PR film was increased with decrease in the $SiO_2$/PR selectivity ratio even though there was not seen an etching shape anomaly such as shoulder loss or bowing.

The above results are summarized in TABLE 1.

TABLE 1

| | Additive | | Etching Test | | | | Iron Conc. | |
|---|---|---|---|---|---|---|---|---|
| | Kind | Conc. [vol. ppm] | $SiO_2$ [nm/min] | SiN [nm/min] | PR | $SiO_2$/PR | on Wafer [atms/cm$^2$] | Etching Shape |
| Example 1 | $CF_3C\equiv N$ | 2 | 80.5 | 128.8 | 23.2 | 3.47 | $6.5 \times 10^{11}$ | good |
| Example 2 | $CF_3C\equiv N$ | 25 | 81.2 | 129.9 | 23.7 | 3.43 | $4.2 \times 10^{11}$ | good |
| Example 3 | $CF_3C\equiv N$ | 129 | 82.5 | 132.0 | 22.9 | 3.60 | $3.1 \times 10^{11}$ | good |
| Example 4 | $CF_3C\equiv N$ | 1231 | 80.1 | 128.2 | 23.5 | 3.40 | $3.3 \times 10^{11}$ | good |
| Example 5 | $CF_3C\equiv N$ | 7927 | 80.9 | 129.8 | 24.5 | 3.31 | $4.1 \times 10^{11}$ | good |
| Example 6 | $CF_3C\equiv N$ | 9328 | 81.0 | 130.2 | 25.4 | 3.19 | $3.6 \times 10^{11}$ | good |
| Example 7 | $CF_3CF_2C\equiv N$ | 235 | 74.6 | 131.0 | 21.8 | 3.43 | $3.1 \times 10^{11}$ | good |
| Comparative Example 1 | — | <0.1 | 80.9 | 129.4 | 23.5 | 3.44 | $4.8 \times 10^{12}$ | good |
| Comparative Example 2 | $CF_3C\equiv N$ | 25936 | 81.4 | 132.5 | 27.8 | 2.92 | $3.6 \times\times 10^{11}$ | selectivity deterioration |
| Comparative Example 3 | $CF_3C\equiv N$ | 111608 | 80.5 | 145.1 | 44.3 | 1.82 | $2.8 \times 10^{11}$ | shoulder loss |
| Comparative Example 4 | $CF_3C\equiv CH$ | 28 | 81.1 | 137.9 | 22.9 | 3.54 | $5.6 \times 10^{12}$ | good |
| Comparative Example 5 | $CH_3C\equiv N$ | 8523 | 75.2 | 128.1 | 28.2 | 2.67 | $8.9 \times 10^{11}$ | selectivity deterioration |

In Comparative Examples 1 and 4, the etching characteristics were favorable. However, an iron component was detected on the wafer in each of these Comparative Examples. The reason for this is assumed to be that the suppression of iron contamination on the wafer by the C2-C3 fluorine-containing linear nitrile compound was not effected. On the other hand, the iron contamination was reduced to a very low level by the addition of $CF_3C\equiv N$ or $CF_3CF_2C\equiv N$ to $CF_3I$ as is seen from the results of Examples 1 to 7. Although there is some unclear point in the process of suppressing corrosion of the storage container, the reason for such low iron contamination is assumed to be that: a passivation film was formed from the fluorine-containing linear nitrile compound on an inner surface of the storage container so as to prevent elution of iron component from the storage container; the vapor pressure of any substance serving as a source of iron contamination in the $CF_3$ was significantly decreased by the fluorine-containing linear nitrile compound; or the fluorine-containing linear nitrile compound had the effect of suppressing deposition of iron component on the wafer.

When the fluorine-containing linear nitrile compound was added to the $CF_3I$, the etching selectivity ratio of the $SiO_2$ or SiN film relative to the PR film was varied with the amount of the fluorine-containing linear nitrile compound added. In each Example, the etching selectivity ratio of the $SiO_2$ film relative to the PR film (referred to as "$SiO_2$/PR etching selectivity ratio") was sufficient. More specifically, the $SiO_2$/PR etching selectivity ratio was at a high level exceeding 3 in each of Examples 1 to 7 in which the amount of the fluorine-containing linear nitrile compound added was less than or equal to 10000 vol. ppm (1 vol %). Further, there did not occur an etching shape anomaly during the hole pattern etching. It can thus be said that it was possible to attain favorable etching characteristics by adding the fluorine-containing linear nitrile compound in an amount ranging from 1 vol. ppm to 10000 vol. ppm to the $CF_3I$.

In the case where $CF_3C\equiv N$ was added in an amount exceeding 10000 vol. ppm as in Comparative Examples 2 and 3, there was seen a remarkable tendency of decrease in the $SiO_2$/PR etching selectivity. In the pattern etching, the etching amount of the resist film was visibly increased. In particular, a surface of the $SiO_2$ film was etched during the pattern etching of Comparative Example 3. It turned out that the performance of the mixed gas as the etching gas was significantly deteriorated with the addition of such a large amount of the fluorine-containing linear nitrile compound.

In the case where a large amount of $CF_3C\equiv N$ was added, nitrogen in the molecule of the additive serves, during the formation of a protective film predominantly composed of $CF_n$ as mentioned above, as an inhibitor of polymerization of $CF_n$ so that the protective film cannot be formed sufficiently. For that reason, it is assumed that the etching of the mask was promoted by $CF_3C\equiv N$, which led to a decrease in the selectivity. It is assumed that this phenomenon would similarly occur in the case of using the other fluorine-containing linear nitrile compound.

In Comparative Example 4, the influence of the additive other than $CF_3C\equiv N$ was studied. In the case of using $CF_3C\equiv CH$, there was not seen the iron contamination suppressing effect as in the case of using $CF_3C\equiv N$.

On the other hand, the influence of the fluorine-free additive other than $CF_3C\equiv N$ was studied in Comparative Example 5. In the case of using $CH_3C\equiv N$, the $SiO_2$/PR etching selectivity ratio was decreased since a protective film predominantly composed of $CF_n$ was not sufficiently formed due to no fluorine content. Furthermore, the iron contamination suppressing effect was smaller than in the case of using $CF_3C\equiv N$.

As described above, the present disclosure enables, in the etching process using $CF_3I$, a reduction in the amount of metal contamination without causing an influence on the etching characteristics.

DESCRIPTION OF REFERENCE NUMERALS

10: Storage container unit
11: Test piece
12: Valve
13: Lid
14: Pressure-resistant vessel
20: Reaction device
21: Chamber 22: Pressure Gauge
23: High-frequency power source
24: Lower electrode
25: Upper electrode
26: Gas introduction port
27: Gas discharge line
28: Test specimen

The invention claimed is:

1. A dry etching method, comprising:
 plasmatizing a dry etching agent supplied from a metallic storage container to provide a plasmatized dry etching agent; and
 etching a silicon oxide or a silicon nitride on a substrate with the plasmatized dry etching agent,
 wherein the dry etching agent stored in the storage container comprises $CF_3I$ and a fluorine-containing linear nitrile compound of 2 or 3 carbon atoms, and
 wherein a concentration of the fluorine-containing linear nitrile compound relative to the $CF_3I$ is higher than or equal to 1 vol. ppm and lower than or equal to 1 vol %.

2. The dry etching method according to claim 1, wherein the fluorine-containing linear nitrile compound of 2 or 3 carbon atoms is $CF_3C{\equiv}N$ or $CF_3CF_2C{\equiv}N$.

3. The dry etching method according to claim 1, wherein the dry etching agent comprises an additive gas, and
 wherein the additive gas is at least one kind of gas selected from the group consisting of $O_2$, $O_3$, $CO$, $CO_2$, $COCl_2$, $COF_2$, $CF_2(OF)_2$, $CF_3OF$, $NO_2$, $NO$, $F_2$, $NF_3$, $Cl_2$, $Br_2$, $I_2$ and $YF_n$ where Y is Cl, Br or I; and n is an integer satisfying $1 \leq n \leq 7$.

4. The dry etching method according to claim 1, wherein the dry etching agent comprises an additive gas, and
 wherein the additive gas is at least one kind of gas selected from the group consisting of $H_2$, HF, HI, HBr, HCl, $NH_3$, $CF_4$, $CF_3H$, $CF_2H_2$, $CFH_3$, $C_2F_6$, $C_2F_4H_2$, $C_2F_5H$, $C_3F_8$, $C_3F_7H$, $C_3F_6H_2$, $C_3F_5H_3$, $C_3F_4H_4$, $C_3F_3H_5$, $C_3F_5H$, $C_3F_3H$, $C_4H_8$, $C_4F_6$, $C_5F_8$, $C_5F_{10}$, $C_3F_6$, $C_3HF_5$, $C_3H_2F_4$ and $C_3H_3F_3$.

5. The dry etching method according to claim 1, wherein the dry etching agent further comprises an inert gas, and
 wherein the inert gas is selected from the group consisting of $N_2$, He, Ar, Ne, K and Xe.

6. A storage container made of a metal material and closed and filled with a mixture comprising $CF_3I$ and a fluorine-containing linear nitrile compound of 2 or 3 carbon atoms, wherein a concentration of the fluorine-containing linear nitrile compound relative to the $CF_3I$ is higher than or equal to 1 vol. ppm and lower than or equal to 1 vol %.

7. The storage container according to claim 6, wherein the storage container is made of manganese steel or stainless steel.

8. The dry etching method according to claim 1, wherein the amount of iron deposit on the substrate after the etching is $6.5 \times 10^{11}$ atms/cm$^2$ or less.

* * * * *